United States Patent [19]

Sanchez

[11] Patent Number: 4,634,753
[45] Date of Patent: Jan. 6, 1987

[54] HYDROXY-T-ALKYL PEROXYESTER

[75] Inventor: Jose Sanchez, Grand Island, N.Y.

[73] Assignee: Pennwalt Corporation, Philadelphia, Pa.

[21] Appl. No.: 717,756

[22] Filed: Mar. 29, 1985

Related U.S. Application Data

[62] Division of Ser. No. 496,357, May 20, 1983, Pat. No. 4,525,308.

[51] Int. Cl.$^4$ .......................... C08F 2/00; C08F 4/32; C08F 4/38
[52] U.S. Cl. ................................ 526/216; 526/232.5; 526/227; 526/232; 525/447
[58] Field of Search ...................... 526/216, 232.5, 232; 525/447

[56] References Cited

U.S. PATENT DOCUMENTS 4,079,074 3/1978 Sanchez .......................... 260/453 R
4,486,580 12/1984 Sanchez ............................. 526/232

Primary Examiner—Joseph L. Schofer
Assistant Examiner—Peter F. Kulkosky

[57] ABSTRACT

Hydroxy-t-akyl peroxyesters having the general structure

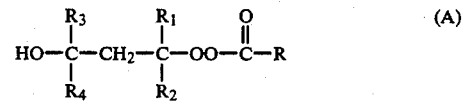

where R, $R_1$, $R_2$, $R_3$ and $R_4$ can be alkyl moieties and having 10 hour half-life temperatures below about 75° C. (for example, 3-hydroxy-1,1-dimethylbutyl peroxyneodecanoate) are used as initiators for vinyl monomer polymerization and as catalysts for curing unsaturated polyester resins in order to improve the efficiency of the systems.

5 Claims, No Drawings

HYDROXY-T-ALKYL PEROXYESTER

This is a divisional of co-pending application Ser. No. 496,357 filed on May 20, 1983, now U.S. Pat. No. 4,525,308.

BACKGROUND OF THE INVENTION

This invention relates to novel hydroxy-t-alkyl peroxyesters (A) and the use of these compositions as free-radical initiators for improved vinyl monomer polymerization processes and as curing catalysts for improved unsaturated polyester resin curing processes.

From an economic standpoint the polymer industry wishes to increase production of polymeric resins without resorting to building additional expensive production facilities. It is well known in the polymerizations arts, especially in the art of polymerizing vinyl chloride, that rates of polymerizations can be enhanced by using more active free-radical catalysts; thus, polymerization cycle times can be decreased and production capacity can be increased when this technique is employed. This phenomenon is especially useful in vinyl chloride polymerizations, since more active catalysts result in higher polymerization rates without simultaneously affecting polymer molecular weight characteristics (assuming that the temperature is not changed); hence, polymer physical properties remain unchanged. It is, also, well known in the peroxide art that half-life characteristic (a measure of peroxide activity) of peroxides can be changed significantly for certain classes of peroxides by employing various structural changes in the peroxide.

The hydroxy-t-alkyl peroxyesters of the present invention have been found to improve the efficiency of polymerization systems using lesser amounts of the initiator than were used in the prior art. The 10 hour half-life temperatures of compounds of the present invention are significantly decreased over similar prior art peroxyesters.

SUMMARY OF THE INVENTION

The present invention is directed to (A) A hydroxy-t-alkyl peroxyester of structure (A)

$$\underset{R_4}{\overset{R_3}{\underset{|}{\text{HO}-\text{C}-\text{CH}_2-\overset{R_1}{\underset{R_2}{\underset{|}{\text{C}}}}-\text{OO}-\overset{\text{O}}{\overset{\|}{\text{C}}}-\text{R}}}} \quad (A)$$

which has a 10 hour half-life temperature below about 75° C., where $R_1$ and $R_2$ are selected from an alkyl of 1 to 4 carbons,
$R_3$ and $R_4$ are selected from hydrogen or an alkyl of 1 to 4 carbons,
$R_1$ and $R_3$ can be connected together to form a lower alkyl substituted 3 carbon alkylene bridge and $R_3$ can additionally be

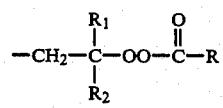

and
R is selected from

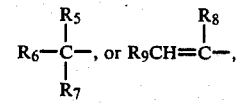

where
$R_5$ is selected from hydrogen or an alkyl of 1 to 8 carbons,
$R_6$ is selected from an alkyl of 1 to 8 carbons,
$R_7$ is selected from the group consisting of an alkyl of 1 to 8 carbons, an alkenyl of 1 to 8 carbons, an aryl of 6 to 10 carbons, an alkoxy of 1 to 6 carbons and an aryloxy of 6 to 10 carbons, and
$R_8$ and $R_9$ are selected from an alkyl 1 to 4 carbons;
(B) A process of polymerizing ethylenically unsaturated monomers (such as ethylene and vinyl chloride) by using an initiating amount of the hydroxy-t-alkyl peroxyester of structure A as the initiator at appropriate temperature during the polymerization; and
(C) A process of curing unsaturated polyester resin compositions by heating such resins in the presence of a catalyzing amount of A as the curing agents.

DETAILED DESCRIPTION OF THE INVENTION

Preparations of the Hydroxy-t-Alkyl Peroxyesters

The hydroxy-t-alkyl peroxyesters (A) of this invention can be prepared by reacting an appropriate acid chloride, acid bromide or acid anhydride with a hydroxy-t-alkyl hydroperoxide in the presence of a base and optionally in the presence of a phase transfer catalyst (PTC). Surprisingly the acylation reaction predominantly occurs at the hydroperoxy group rather than at the hydroxy group of the hydroxy-t-alkyl hydroperoxide, thus forming the invention hydroxy-t-alkyl peroxyesters A rather than hydroperoxy-alkyl esters B. Some further reaction of A with the acylating

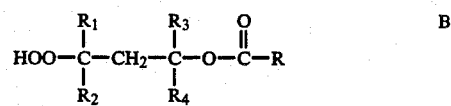

agent can occur to produce small amounts of ester-t-alkyl peroxyester C. C could also be produced to a small extent by further reaction

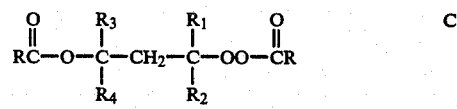

of B (if it formed) with acylating agent. In general, the acid chlorides employed for producing the hydroxy-t-alkyl peroxyesters of this invention are sterically hindered acid chlorides which readily react at the hydroperoxy group of the hydroxy-t-alkyl hydroperoxide but much less readily react at the hydroxy group of the hydroxy-t-alkyl hydroperoxide or at the hydroxyl group of A. Such hindered acid chlorides are derived from hindered di- and tri-α-branched carboxylic acids that are listed further below. Less sterically hindered acid chlorides, such as those derived from non- and mono-α-branched carboxylic acids and aromatic carboxylic acids readily react with the hydroxy group of the hydroxy-t-alkyl peroxyester (see Example 17, infra).

The invention hydroxy-t-alkyl peroxyesters of this invention are restricted to those derived from sterically hindered acid chlorides as defined above. This puts an upper 10 hour half-life temperature limit of about 75° C. on the invention hydroxy-t-alkyl peroxyesters since one of the higher temperature invention hydroxy-t-alkyl peroxyesters, 3-hydroxy-1,1-dimethylbutyl peroxy-(2-ethylhexanoate), had a 10 hour half-life temperature of about 66°–67° C. The non-invention hydroxy-t-alkyl peroxyesters that are derived from less hindered acid chlorides generally would have 10 hour half-life temperatures of about 90° to 100° C. (if they could be made). Hence, the invention hydroxy-t-alkyl peroxyesters (Structure A) are much more active in initiating polymerizations of ethylenically unsaturated monomers and in curing of unsaturated polyester resins. The preferred acid chlorides can be prepared from the corresponding acid by reacting with acid chlorinating agents such as $PCl_3$, $POCl_3$, $PCl_5$, $SOCl_2$, phosgene (in the presence of N,N-dimethylformamide) and benzotrichloride followed by isolation of the acid chloride product from the reaction mixture.

Carboxylic acids that are useful for producing the hydroxy-t-alkyl peroxyester A of this invention include alkylarylacetic acids such as 2-phenylpropionic acid 2-phenylbutyric acid, and 2-methyl-2-phenylpropionic acid, alkoxypropionic acids such as 2-methoxypropionic acid, aryloxypropionic acids such as 2-phenoxypropionic acid, unsaturated carboxylic acids such as methacrylic acid and 2-methyl-2-butenoic acid, α,α-dialkylacetic acids such as isobutyric acid, 2-ethylbutyric acid, 2-ethylhexanoic acid, and 2-butyloctanoic acid and α,α,α-trialkylacetic acids (i.e., neoacids) such as pivalic acid, neohexanoic acid, neoheptanoic acid, neooctanoic acid, neononanoic acid, neodecanoic acid and neotridecanoic acid (the compositions and structures of the latter five neoacid mixtures being those described in U.S. Pat. No. 3,624,123).

Hydroxy-t-alkyl hydroperoxides that are useful for producing the hydroxy-t-alkyl peroxyesters A of this invention include 3-hydroxy-1,1-dimethylpropyl hydroperoxide, 3-hydroxy-1,1-dimethylbutyl hydroperoxide, 1-ethyl-3-hydroxy-1-methylpentyl hydroperoxide, 1,1-diethyl-3-hydroxybutyl hydroperoxide, 5-hydroxy-1,3,3-trimethylcyclohexyl hydroperoxide and 4-hydroxy-2,6-dimethyl-2,6-dihydroperoxyheptane. The hydroxy-t-alkyl hydroperoxides can be prepared by treating the corresponding hydroxy-t-alkanols with excess hydrogen peroxide in the presence of a strong acid catalyst such as sulfuric acid, phosphoric acid, perchloric acid, the acid form of an ion exchange resin or p-toluenesulfonic acid. For instance, 1,1-dimethyl-3-hydroxybutyl hydroperoxide, also know as hexylene glycol hydroperoxide, has been prepared in this manner from commericially available 2-methyl-2,4-pentanediol (hexylene glycol) according to U.S. Pat. No. 3,236,872. The hydroxy-t-alkanols which are used to prepared the hydroxy-t-alkyl hydroperoxides can be prepared by methods well known in the art. For instance, some hydroxy-t-alkanols can be prepared by treating lactones with a Grignard agent (e.g., methylmagnesium bromide). The hydroxy-t-alkyl hydroperoxides can also be prepared using the corresponding hydroxy-t-alkylene in place of the hydroxy-t-alkanols. Thus, treatment of a hydroxy-t-alkylene with hydrogen peroxide in the presence of a strong acid catalyst results in formation of the hydroxy-t-alkyl hydroperoxide.

The bases that are useful in preparing the hydroxy-t-alkyl peroxyesters A of this invention include inorganic bases such as NaOH, KOH, LiOH, $Na_2CO_3$ and $K_2CO_3$ and organic amines such as pyridine, N,N-dimethylaniline, triethylamine, tributylamine and 1,4-diazabicyclo[2.2.2]octane. The optionally empolyed phase transfer catalysts include tetraalkylammonium salts such as tetrabutylammonium chloride, bromide and hydrogen sulfate and other reported phase transfer catalysts.

Representative of the hydroxy-t-alkyl peroxyester A of this invention are as follows:
3-Hydroxy-1,1-dimethylbutyl peroxy-2-phenylbutyrate,
3-Hydroxy-1,1-dimethylbutyl peroxy-2-phenoxypropionate,
3-Hydroxy-1,1-dimethylbutyl peroxymethacrylate,
3-Hydroxy-1,1-dimethylbutyl peroxy-2-methylcrotonate,
3-Hydroxy-1,1-dimethylbutyl peroxyisobutyrate,
3-Hydroxy-1,1-dimethylbutyl peroxy-(2-ethylhexanoate),
3-Hydroxy-1,1-dimethylbutyl peroxy-(2-butyloctanoate),
3-Hydroxy-1,1-dimethylbutyl peroxypivalate,
3-Hydroxy-1,1-dimethylbutyl peroxyneohexanoate,
3-Hydroxy-1,1-dimethylbutyl peroxyneoheptanoate,
3-Hydroxy-1,1-dimethylbutyl peroxyneodecanoate,
3-Hydroxy-1,1-dimethylbutyl peroxyneotridecanoate,
3-Hydroxy-1,1-dimethylpropyl peroxyneohexanoate,
3-Hydroxy-1,1-dimethylpropyl peroxyneodecanoate,
3-Hydroxy-1,1-dimethylpropyl peroxypivalate,
3-Hydroxy-1,1-diethylbutyl peroxyneohexanoate,
5-Hydroxy-1,3,3-trimethylcyclohexyl peroxyneodecanoate,
4-Hydroxy-2,6-dimethyl-2,6-di(neohexanoylperoxy)-heptane, and
4-Hydroxy-2,6-dimethyl-2,6-di(neodecanoylperoxy)-heptane.

Vinyl Polymerizations

In the free-radical polymerizations or copolymerizations of ethylenically unsaturated monomer at suitable temperatures (and pressures) the hydroxy-t-alkyl peroxyesters A of this invention are found to be efficient initiators (i.e., reduced initiator requirements).

Ethylenically unsaturated monomers include olefins, such as ethylene, propylene, styrene, alpha-methylstyrene, chlorostyrene, vinyltoluene, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid, methacrylic acid and their esters and amides, such as methyl, ethyl, n-butyl and 2-ethylhexyl acrylates and methacrylates, and acrylamide and methacrylamide; maleic anhydride; maleic and fumaric acids and their esters; vinyl halo and vinylidene halo compounds, such as, vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, diallyl phthalate, allyl ethyl carbonate, triallyl phosphate, diallyl fumarate and diallyl carbonate; acrolein; methyl vinyl ketone; and mixtures thereof.

In this invention temperatures of 20° C. to 250° C., preferably 30° to 200° C., and peroxyester levels (on a pure baise) of 0.002 to 3%, preferably 0.002 to 1% by weight based on monomer, are employed in polymerizations or copolymerizations of ethylenically unsaturated monomers.

The hydroxy-t-alkyl peroxyesters A of this invention can also be used in combination with other free-radical initiators such as peroxyesters which include t-butyl peroxypivalate, t-butyl peroxy-2-ethylhexanoate, t-butyl peroxyacetate, t-amyl peroxypivalate, t-butyl peroxyneodecanoate, t-amyl peroxyneodecanoate, 1,1,3,3-tetramethylbutyl peroxyneodecanoate and alpha-cumyl peroxyneodecanoate; dialkyl peroxydicarbonates including di- n-propyl, diisopropyl, di-(sec-butyl), dicyclohexyl, di-(4-t-butylcyclohexyl), di-(2-phenoxyethyl), di-(2-ethylhexyl) and dihexadecyl peroxydicarbonates; acyl alkylsulfonyl peroxides including acetyl cyclohexylsulfonyl peroxide and acetyl sec-heptylsulfonyl peroxide; diacyl peroxides including dibenzoyl peroxide, didodecyl peroxide, diisobutyryl peroxide and di-(2-methylpentanoyl)peroxide; diperoxyketals including 2,2-di-(t-butylperoxy)butane; 2,2-di-(t-butylperoxy)heptane, ethyl 3,3-di-(t-butylperoxy)-butyrate, 1,1-di-(t-butylperoxy)-3,3,5-trimethylcyclohexane, 1,1-di-(t-butylperoxy)cyclohexane and 1,1-di(t-amylperoxy)cyclohexane; monoperoxycarbonates including OO-t-butyl O-isopropyl monoperoxycarbonate and OO-t-butyl O-(2-ethylhexyl)monoperoxycarbonate; dialkyl peroxides such as 2,5-dimethyl-2,5-di-(t-butylperoxy)hexane; and azo compounds including azobis(isobutyronitrile), 2-t-butylazo-2-cyano-4-methoxy-4-methylpentane and 1-t-butylazo-1-cyanocyclohexane.

CURING OF UNSATURATED POLYESTER RESINS

In the curing of unsaturated polyester resin compositions by heating at suitable curing temperatures in the presence of free-radical curing agents, the hydroxy-t-alkyl peroxyesters A of this invention exhibit enhanced curing activity. Unsaturated polyester resins that can be cured by the peroxides of this invention usually includes an unsaturated polyester and one or more polymerizable monomers.

The unsaturated polyesters are, for instance, polyesters as they are obtained by esterifying at least one ethylenically unsaturated di- or polycarboxylic acid, anhydride or acid-halide, such as maleic acid, fumaric acid, glutaconic acid, itaconic acid, mesaconic acid, citraconic acid, allylmalonic acid, allylsuccinic acid, tetrahydrophalic acid and others with saturated or unsaturated di- or polyols, such as ethylene glycol, diethylene glycol, triethylene glycol, 1,2- and 1,3-propanediols, 1,2- 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,2,4-trimethyl-1,3-pentanediol, glycerol, pentaerythritol, mannitol and others. Mixtures of such polyacids and/or mixtures of such polyalcohols may also be used. The unsaturated di- or polycarboxylic acids may be partially replaced, by saturated polycarboxylic acids, such as adipic acid, succinic acid, sebacic acid and others and/or by aromatic polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, 5,6-dicarboxy-1,2,3,4,7,7-hexachlorobicyclo(2.2.1)-2-heptene and others.

The other component of the unsaturated polyester resin composition, the polymerizable monomer or monomers, can be preferably ethylenically unsaturated monomers, such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate and others, or mixtures thereof, which are copolymerizable with said polyesters.

A preferred resin composition contains as the polyester component the esterification product of 1,2-propylene glycol (a polyalcohol), maleic anhydride (an anhydride of an unsaturated polycarboxylic acid) and phthalic anhydride (an anhydride of an aromatic dicarboxylic acid) as well as the monomer component, styrene.

Temperatures of about 20° C. to 200° C. and peroxide levels of about 0.05% to 5% or more by weight of curable unsaturated polyester resin are normally employed.

The unsaturated polyesters described above can be filled with various materials such as sulfur, glass fibers, carbon blacks, silicas, metal silicates, clays, metal carbonates, antioxidants, heat and light stabilizers, sensitizers, dyes, pigments, accelerators, metal oxides such as zinc oxide, blowing agents, etc.

Other types of unsaturated resins can be cured using the compositions of this invention as curing catalysts. These resins, called unsaturated vinyl ester resins, consist of a vinyl ester resin component and one or more polymerizable monomer components. The vinyl ester resin component can be made by reacting a chloroepoxide such as epichlorohydrin with appropriate amounts of a glycol such as bisphenol A [2,2-di-(4-hydroxyphenyl)propane], in the presence of a base such as sodium hydroxide, to yield a condensation product having terminal epoxy groups derived from epichlorohydrin. Subsequent reaction of the condensation product with polymerizable unsaturated carboxylic acids such as acrylic acid and methacrylic acid, in the presence or absence of acidic or basic catalysts, results in formation of a vinyl ester terminated resin component. Normally styrene is added as the polymerizable monomer component to complete the preparation of the unsaturated vinyl ester resin.

Temperatures of about 20° C. to 200° C. and pure peroxide levels of about 0.05% to 5% or more by weight of curable unsaturated vinyl ester resin compositions are normally employed for curing of the unsaturated vinyl ester resins.

The unsaturated vinyl ester resin described above can be filled with the materials employed with the unsaturated polyester resin compositions described previously.

The hydroxy-t-alkyl peroxyesters A of this invention can also be employed for curing of monomers such as diethylene glycol bis(allyl carbonate) (ADC) as well as other diallyl and polyallyl compounds. In these applications 0.1 to 10% or more of the invention peroxyesters, based on curable monomer, can be employed. Temperature profiles are usually employed in the ADC curing processes. The temperatures range from about 70° C. initially to about 125° C. and the time for curing can range up to 10 hours.

The hydroxy-t-alkyl peroxyesters A of this invention can also be used as intermediates to prepare other peroxides by reaction at the hydroxy group.

EXAMPLES

Neohexanoyl chloride and other acid chlorides used in the preparations of the hydroxy-t-alkyl peroxyesters of this invention, prior art peroxyesters, and other peroxyesters prepared in the examples were prepared by procedures similar to that outlined in Example I of U.S. Pat. No. 3,624,123. 3-Hydroxy-1,1-dimethylbutyl hydroperoxide was prepared according to the procedure outlined in Example 2 of U.S. Pat. No. 3,236,872. 7-Hydroxy-1,1,5-trimethylheptyl hydroperoxide was similarly prepared.

The starting material, 3-hydroxy-1,1-dimethylpropyl hydroperoxide, was prepare using a procedure similar for preparing 3-hydroxy-1,1-dimethylbutyl hydroperoxide, mentioned above; this compound was prepared from 3-methyl-3-buten-1-ol (0.50 mole) and 50% $H_2O_2$ (2.00 moles) with concentrated $H_2SO_4$ (0.75 mole) as the acid catayst. The product that was isolated was a liquid having an assay of 81.2% according to hydroperoxide active oxygen content. The corrected yield was 37.9%.

EXAMPLE 1

TABLE I

| 1-Hydroxy-1,1-Dimethylbutyl peroxyester | | Acid Chloride Employed | Peroxidation Conditions | | | Assay, % | Corr. Yield, % | Infrared OH Band, cm$^{-1}$ |
|---|---|---|---|---|---|---|---|---|
| | | | Temp., °C. | Time, hrs | PTC | | | |
| Peroxypivalate | (I-1) | Pivaloyl | −5 to −2 | 2.0 | TBABr* | 72.3 | 81.3 | broad, 3450–3550 |
| Peroxyneohexanoate | (I-2) | Neohexanoyl | 0 to 5 | 2.0 | No | 80.5 | 79.8 | broad, 3450–3550 |
| Peroxyneohexanoate | (I-2) | Neohexanoyl | 0 to 5 | 2.0 | TBABr* | 77.9 | 90.7 | broad, 3450–3550 |
| Peroxyneodecanoate | (I-3) | Neodecanoyl | 28 to 30 | 1.0 | No | 79.3 | 78.5 | broad, 3450–3550 |
| Peroxyneodecanoate | (I-3) | Neodecanoyl | 28 to 30 | 1.0 | TBABr* | 81.8 | 73.8 | broad, 3450–3550 |
| Peroxyneotridecanoate | (I-4) | Neotridecanoyl | 28 to 30 | 1.0 | No | 67.5 | 73.7 | medium, 3500 |
| Peroxyisobutyrate | (I-5) | Isobutyryl | 30 | 1.0 | No | 80.2 | 56.6 | broad, 3400–3500 |
| Peroxy-2-ethylhexanoate | (I-6) | 2-Ethylhexanoyl | 10 to 15 | 0.5 | No | 85.6 | 84.3 | sharp, 3550 |
| Peroxy-2-phenylbutyrate | (I-7) | 2-Phenylbutyryl | 10 to 15 | 0.5 | No | 74.1 | 50.0 | — |

*TBABr — Tetrabutylammonium Bromide, Phase Transfer Catalyst (PTC)

Preparation of 3-Hydroxy-1,1-dimethylbutyl Peroxypivalate (I-1)

A jacketed reactor equipped with a mechanical stirrer, a thermometer and a dropping funnel was charged with 19.9 g (0.160 mole) of 45% KOH, 9.9 g of water, 21.5 g (0.150 mole) of 93.7% 3-hydroxy-1,1-dimethyl butyl hydroperoxide (also known as 4-hydroxy-2-methyl-2-hydroperoxypentane), 25 g of methylene chloride and 0.65 g (0.002 mole) of tetrabutylammonium bromide, a phase transfer catalyst (PTC). The resulting vigorously stirred mixture was cooled to −5° to −2° C. and to it was slowly added 12.6 g (0.100 mole) of 95.4% pivaloyl chloride over a period of about 30 minutes. The resulting product mixture was then stirred for 2 hours at −5° to −2° C. after which 25 g of 10% KOH and an additional 50 g of methylene chloride were added to the reaction mixture. The reaction mass was allowed to separate into two liquid phases at 10° C. and the lower organic layer was removed, dried over about 5% by weight of anhydrous $MgSO_4$ and after the spent desiccant was separated by filtration the methylene chloride was removed in vacuo at 0° to 10° C. Obtained was 24.5 g of liquid product which had an assay of 72.3% according to peroxyester active oxygen content. The corrected yield was 81.3%. An infrared spectrum of the product showed a large broad OH band centered at 3450 to 3550 cm$^{-1}$.

EXAMPLE 2

Preparations of Other 3-Hydroxy-1,1-dimethylbutyl Peroxyesters

The procedure utilized in Example 1 was employed for preparation of other 3-hydroxy-1,1-dimethylbutyl peroxyesters from 3-hydroxy-1,1-dimethylbutyl hydroperoxide and various carboxylic acid chlorides. The starting carboxylic acid chloride, the conditions employed and the yield data for these preparations are summarized in Table I. Also included in Table I are the results for Example 1. In all cases, the infrared spectrum of the product exhibited a strong and broad OH band centered at about 3400 to 3500 cm$^{-1}$ which showed that the desired product was obtained.

Decomposition studies in dilute solution showed that 3-hydroxy-1,1-dimethylbutyl peroxyneodecanoate (I-3) had a 10 hour half-life temperature (i.e., the temperature at which half of the peroxide is decomposed in 10 hours) in trichloroethylene of 36° C. and that 3-hydroxy-1,1-dimethylbutyl peroxy-(2-ethylhexanoate)-(I-6) had a 10 hour half-life temperature in benzene of about 66° to 67° C.

For the sake of comparision, some of the next adjacent homologue compounds where the atomic distance (as measured by intervening atoms) between the hydroxyl function and the peroxyester function is increased by a carbon atom were prepared as follows:

Preparation of 7-Hydroxy-1,1,5-trimethylheptyl Peroxypivalate (C-1)

A jacketed reactor equipped with a mechanical stirrer, a thermometer and a dropping funnel was charged with 9.3 g (0.075 mole) of 45% KOH, 4.7 g of water and 11.3 g (0.058 mole) of 97.3% 7-hydroxy-1,1,5-trimethylheptyl hydroperoxide. To this vigorously stirred solution at 30° C. was slowly added 6.4 g (0.050 mole) of 94.3% pivaloyl chloride over a period of 20 minutes. The resulting mixture was then vigorously stirred for one hour at 30° C. after which it was cooled to 15° C. and 100 ml of pentane and 25 ml of water were added. After separating and discarding the aqueous phase the product solution was washed at 10° to 15° C. with 20 g of buffered sodium sulfite solution (consisting of 0.8 g of acetic acid, 1.2 g of sodium acetate, 2.0 g of sodium sulfite and 16 g of water), with 15 ml of water and then with 20 g of 7.7% sodium hydrogen carbonate solution. The resulting pentane solution was then dried over anhydrous $MgSO_4$ and after separation of the spent desiccant by filtration the pentane was removed in vacuo at 0° to 10° C. leaving 8.2 g of liquid product. The assay of the product according to peroxyester active oxygen was 69.6% and the corrected yield was 41.7%.

An infrared spectrum of the product showed a strong, broad OH band centered at 3400 to 3500 cm$^{-1}$.

Preparation of 7-Hydroxy-1,1,5-trimethylheptyl Peroxyneodecanoate (C-2)

The same procedure as used in the preparation of C-1, supra, was employed for the preparation of 7-hydroxy-1,1,5-trimethylheptyl peroxyneodecanoate using as the starting materials 7-hydroxy-1,1,5-trimethylheptyl hydroperoxide and neodecanoyl chloride. The liquid product was obtained in 84.3% assay and 72.5% corrected yield. An infrared spectrum of the product showed a strong, broad OH band centered at 3400 to 3500 cm$^{-1}$.

Preparation of 7-Hydroxy-1,1,5-trimethylheptyl Peroxyneohexanoate (C-3)

Employing the reactants 7-hydroxy-1,1,5-trimethylheptyl hydroperoxide and neohexanoyl chloride and using the same procedure as used for the preparation of C-1, the title peroxyester, 7-hydroxy-1,1,5-trimethylheptyl peroxyneohexanoate, was prepared in an assay of 86.1% and a corrected yield of 71%. An infrared spectrum of the product showed a very large OH band centered at about 3450 cm$^{-1}$.

Preparation of 7-Hydroxy-1,1,5-trimethylheptyl Peroxy(2-Ethylhexanoate) (C-4)

The title peroxyester, 7-hydroxy-1,1,5-trimethylheptyl peroxy-(2-ethylhexanoate), was prepared in an assay of 88.7% and a corrected yield of 78.0% by using the procedure employed in the preparation of C-1 using as reactants 7-hydroxy-1,1,5-trimethylheptyl hydroperoxide and 2-ethylhexanoyl chloride. An infrared spectrum of the product showed a moderate OH band centered at about 3450 to 3500 cm$^{-1}$.

Preparation of 4-Hydroxy-1,1,4,4-Tetramethylbutyl Peroxypivalate (C-5)

A jacketed reactor equipped with a mecahnical stirrer, a thermometer and a dropping funnel was charged with 18.7 g (0.150 mole) of 45% KOH, 15.0 g of water, 27.6 (0.120 mole) of 77.6% (wetted solid) 2,5-dimethyl-2,5-dihydroperoxyhexane and 100 ml of methylene chloride. To the resulting two liquid phase mixture at 28° to 30° C. was added 12.8 g (0.100 mole) of 94.3% pivaloyl chloride over a period of about 30 minutes. The resulting mixture was then stirred for 2.0 hours at 28° to 30° C. after which the mixture was cooled to 15° to 20° C. and was allowed to separate into phases. The upper aqueous layer was removed and was discarded. The resulting product solution was then washed with 50 ml of 20% KOH solution at 0° C. and then with 50 ml of 7.7% sodium hydrogen carbonate solution at 15° to 20° C. The methylene chloride solution was then cooled to 0° to 10° C. and was reacted with 187 g of buffered sodium sulfite solution (consisting of 7.6 g of acetic acid, 8.4 g of sodium acetate, 19 g of sodium sulfite and 152 g of water) in order to covert the 4-hydroperoxy-1,1,4,4-tetramethylbutyl peroxypivalate that was formed in the peroxidation reaction to 4-hydroxy-1,1,4,4-tetramethylbutyl peroxypivalate, the desired product. A thick emulsion resulted which required three days of storage in the refrigerator to separate into two liquid phases. The upper aqueous layer was removed and an equal volume of diethyl ether was added in order to facilitate further processing. The solution was dried over anhydrous MgSO$_4$ and after separation of the spent desiccant by filtration the solvents were remove in vacuo at 0° to 10° C. Some solids were removed by filtration and the resulting liquid weighed 20.4 g. The assay of the product was 90.3% according to peroxyester active oxygen content. The corrected yield was 74.9%. An infrared spectrum of the product showed a broad OH band centered at 3300 to 3400 cm$^{-1}$.

Preparation of 4-Hydroxy-1,1,4,4-Tetramethylbutyl Peroxyneodecanoate (C-6)

Reacting neodecanoyl chloride with 2,5-dimethyl-2,5-dihydroperoxyhexane followed by reducing the intermediate product with a buffered sodium sulfite solution employing the same procedure as used in preparation of C-5 resulted in the preparation of 4-hydroxy-1,1,4,4-tetramethylbutyl peroxyneodecanoate. The liquid product had an assay of 91.7% and was obtained in a corrected yield of 55.1%. An infrared spectrum of the product showed a broad OH band centered at 3300 to 3500 cm$^{-1}$.

EXAMPLE 3

Preparation of 3-Hydroxy-1,1-Dimethylpropyl Peroxyneodecanoate (I-8)

The procedure employed for preparation of 3-hydroxy-1,1-dimethylbutyl peroxyneodecanoate in Example 2 (without the PTC) was used in this example for preparing 3-hydroxy-1,1-dimethylpropyl peroxyneodecanoate from neodecanoyl chloride and 3-hydroxy-1,1-dimethylpropyl hydroperoxide. The assay of the product was 66.0% according to peroxyester active oxygen content and the correct yield was 65.1%. The infrared spectrum showed a broad OH band centered at 3350 to 3450 cm$^{-1}$.

EXAMPLE 4

Preparation of 3-Hydroxy-1,1-Dimethylpropyl Peroxyneohexanoate (I-9)

The procedure employed for preparation of 3-hydroxy-1,1-dimethylbutyl peroxyneohexanoate in Example 2 (without the PTC) was used in this example for preparating 3-hydroxy-1,1-dimethylpropyl peroxyneohexanoate from neohexanoyl chloride and 3-hydroxy-1,1-dimethylpropyl hydroperoxide. The assay of the product was 54.3% according to peroxyester active oxygen content and the corrected yield was 42.7%. An infrared spectrum of the product showed a broad OH band centered at 3400 to 3450 cm$^{-1}$.

EXAMPLE 5

Vinyl Chloride Suspension Polymerizations Employing Hydroxy-t-Alkyl Peroxyesters as Free-Radical Initiators Several hydroxy-t-alkyl peroxyesters of the instant invention were comparatively evaluated with art t-butyl peroxyesters derived from the same carboxylic acids in vinyl chloride suspension polymerizations at 50° C. and 55° C. The vinyl chloride suspension polymerization procedure that was employed is described below.

Suspension Polymerizations

Polymerizations of vinyl chloride in suspension were carried out in a 1.5 liter reactor, which was designed and instrumented such that the polymerization could be monitored calorimetrically. The reactor was immersed in a water bath, maintained 0.5° C. above the desired reaction temperature, thus preventing any heat loss to the surroundings. The heat produced from the exothermic polymerization plus the heat passed into the reactor from the water bath were removed by the passage of cooling water through internal coils in the reactor. Thus, the temperature was kept constant. The flow rate of the cooling water and the temperature difference between entrance and exit streams were monitored, thus producing a continuous recording of heat removed (cal. $\text{min}^{-1}$).

The pressure in the reactor was also continuously monitored. At about 70% conversion of monomer to polymer, the monomer in the vapor phase became depleted and the pressure fell. Thus, from a knowledge of the point of 70% conversion and the heat of polymerization of vinyl chloride (23 Kcal/mole), it was possible to calculate the "background count" in the calorimetric recording; this background was due to heat flow from the water bath to the reactor. By substraction, the true rate of polymerization (cal. $\text{min}^{-1}$), as function of time, was obtained.

In the polymerization the following sequence of operations was followed:
(1) The reactor was assembled and tested for leaks.
(2) The water bath around the reactor was heated to 0.5° C. above the desired reaction temperature.
(3) The cooling water bath was heated to 10° C. less than the reaction temperature.
(4) The aqueous phase plus suspending agents (described later) was heated to 10° C. above the desired reaction temperature, and charged into the reactor.
(5) The initiator compositions were added and the filling port sealed.
(6) The reactor was evacuated by the use of a water aspirator.
(7) The vinyl chloride (200 g) was added, by displacement with nitrogen, from a small cylinder, the reactor was pressurized with nitrogen to about 150 psi (guage). The addition of the cold vinyl chloride reduced the temperature of the aqueous phase to a point close to the desire reaction temperature.
(8) Stirring was commenced.
(9) The reactor controllers were switched on beginning automatic control of the temperature and continuous recording of heat output and pressure.
(10) After the pressure drop was observed, the pressure, temperature and heat of polymerization were further monitored for another one to two hours. The reactor data after the pressure drop were then used to determine the rate of pressure drop, $\Delta P/\Delta t$. The $\Delta P/\Delta t$ was an important value since it was a measure of the rate of polymerization after onset of the pressure drop. The larger the absolute value of $\Delta P/\Delta t$ the higher the rate of polymerization after the pressure drop and the higher the percent conversion of vinyl chloride monomer to polyvinyl chloride. After these data were obtained, the remaining vinyl chloride and nitrogen were vented and the reactor dismantled for cleaning.

| Suspension System Used (pH~6.5) | |
|---|---|
| 1% solution of Aerosol MA 80%* | 42 ml |
| 1% solution of Methocel F 50** | 168 ml |
| Triply distilled water | 469 ml |

*Surfactant made by American Cyanamid Co. (sodium dihexyl sulfosuccinate)
**Hydroxypropyl methyl cellulose polymer made by Dow Chemical.
Note: pH of the aqueous phase was measured at ambient temperatures, 22° C., using a standard pH meter.

TABLE II
Vinyl Chloride Suspension Polymerization Efficiencies of Hydroxy-t-Alkyl Peroxyesters

| Peroxyester Employed | Peroxyester Level | | Polymer Conditions | | Time to Press. Drop, MINS | Rate of Press. Drop $\Delta P/\Delta t$, psi/M |
|---|---|---|---|---|---|---|
| | P/HPM[1] | MOLES/HGM[2] | Temp., °C. | pH | | |
| I-1 | 0.075 | $3.44 \times 10^{-4}$ | 55 | ~6.5 | 230 | −12 |
| A-1 | 0.060 | $3.44 \times 10^{-4}$ | 55 | ~6.5 | 440 | −18 |
| I-2 | 0.119 | $5.12 \times 10^{-4}$ | 55 | ~6.5 | 170 | −44 |
| A-2 | 0.096 | $5.10 \times 10^{-4}$ | 55 | ~6.5 | 250 | −20 |
| A-3 | 0.104 | $5.14 \times 10^{-4}$ | 55 | ~6.5 | 240 | −24 |
| I-3 | 0.125 | $4.33 \times 10^{-4}$ | 55 | ~6.5 | 180 | NA* |
| I-3 | 0.099 | $3.42 \times 10^{-4}$ | 50 | ~6.5 | 310 | NA* |
| A-4 | 0.125 | $5.11 \times 10^{-4}$ | 55 | ~6.5 | 270 | −15 to −17 |
| A-5 | 0.132 | $5.11 \times 10^{-4}$ | 55 | ~6.5 | 240 | −17 |
| C-3 | 0.148 | $5.13 \times 10^{-4}$ | 55 | ~6.5 | 300 | −26 |
| C-5 | 0.091 | $3.48 \times 10^{-4}$ | 55 | ~6.5 | >450[3] | NA* |

*NA — not available.
[1]P/HPM — Parts per hundred parts monomer.
[2]MOLES/HGM — Moles per hundred grams monomer.
[3]No pressure drop observed up to 450 minutes.

Table II summarizes the times that were required for reaching the onset of pressure drop [ca. 70% conversion of vinyl chloride monomer to polyvinyl chloride (PVC)] and the rate of pressure drop ($\Delta P/\Delta t$) after onset of the pressure drop when the hydroxy-t-alkyl peroxyesters of this invention, i.e., 3-hydroxy-1,1-dimethylbutyl peroxypivalate (I-1), 3-hydroxy-1,1-dimethylbutyl peroxyneohexanoate (I-2) and 3-hydroxy-1,1-dimethylbutyl peroxyneodecanoate (I-3), were evaluated and compared to the corresponding t-alkyl peroxyesters of the prior art, i.e., t-butyl peroxypivalate (A-1), t-butyl peroxyneohexanoate (A-2), t-amyl peroxyneohexanoate (A-3), t-butyl peroxyneodecanoate (A-4) and t-amyl peroxyneodecanoate (A-5). The time to pressure drop results unexpectedly and surprisingly showed that the hydroxy-t-alkyl peroxyesters of this invention (e.g. I-1, I-2 and I-3) were significantly more efficient on an equal molar basis than were the corresponding t-alkyl peroxyesters of the prior art (e.g., A-1, A-2, A-3, A-4, and A-5, respectively). These results significantly advance the peroxide and the vinyl chloride polymerization art, since hydroxy-t-alkyl peroxyesters of the instant invention are required in significantly lesser amounts than are the corresponding prior art t-alkyl peroxyesters. This means that a PVC producer would not only use significantly less of the hydroxy-t-alkyl peroxyesters of this invention for producing the same amount of PVC (see results in Table II for I-3 vs. A-4 and A-5) but he would also have to store less of the invention hydroxy-t-alkyl peroxyesters in his refrigerated storage facilities. Therefore, the initiator costs to the PVC producer would be considerably reduced if the PVC producer were to employ the more active hydroxy-t-alkyl peroxyesters of this invention for polymerizing vinyl chloride.

Table II also summarizes vinyl chloride suspension efficiency data for two other hydroxy-t-alkyl peroxyesters, 7-hydroxy-1,1,5-trimethylheptyl peroxyneohexanoate (C-3) and 4-hydroxy-1,1,4,4-tetramethylbutyl peroxypivalate (C-5). Comparing the efficiency of invention hydroxy-t-alkyl peroxyester I-2 with that of C-3 and the efficiency of invention hydroxy-t-alkyl peroxyester I-1 with that of C-5, the efficiencies of invention hydroxy-t-alkyl peroxyester I-1 and I-2 were significantly better than were those of C-5 and C-3, respectively. Hence, these results demonstrated the criticalness that the invention hydroxy-t-alkyl peroxyesters must have one carbon atom between the R—C(O)—OO—C(CH$_3$)$_2$— group and the HOCR$_3$R$_4$— group. If two carbons (e.g., C-5) or five carbons (e.g., C-3) are present, the resulting hydroxy-t-alkyl peroxyesters are significantly less efficient than the invention hydroxy-t-alkyl peroxyesters (e.g., I-1 and I-2).

EXAMPLE 6

SPI Exotherms of the Hydroxy-t-Alkyl Peroxyesters of this Invention

The unsaturated polyester resin in this example was a mixture of an unsaturated polyester and styrene monomer. The unsaturated polyester was an alkyd resin made by esterifying the following components:

| Component | Quantity |
| --- | --- |
| Maleic anhydride | 1.0 mole |
| Phthalic anhydride | 1.0 mole |
| Propylene glycol | 2.2 moles |

To the resulting resin was added 0.013% by weight of hydroquinone inhibitor. The alkyd resin had an Acid No. of 45–50. Seven (7) parts by weight of the above polyester (alkyd resin) were diluted with three (3) parts by weight of monomeric styrene. The resulting unsaturated polyester resin had the following properties:

| a. Viscosity (Brookfield No. 2 at 20 r.p.m.) | 13.0 poise |
| --- | --- |
| b. Specific gravity | 1.14 |

Curing Procedure

Gelation and cure characteristics of various initiators in the above unsaturated polyester resin were determined using the Standard SPI Exotherm Procedure ("SPI Procedure for Running Exotherm Curves-Polyester Resins", published in the Preprint of the 16th Annual Conference—Reinforced Plastics Division, Society of the Plastics Industry, Inc. February 1961). Using the procedure at 82° C. several hydroxy-t-alkyl peroxyesters of this invention were evaluated and compared to the results employing prior art t-alkyl peroxyesters derived from the same carboxylic acids. The results are summarized in Table III and show that the hydroxy-t-alkyl peroxyester of this invention, I-1, I-2 and I-3, are more active than the corresponding t-butyl peroxyesters A-1, A-2 and A-4, respectively, of the art as judged by significantly shorter cure times.

TABLE III

82° C. SPI Exotherm Data for Hydroxy-t-Alkyl Peroxyesters
(1.0% by weight of pure peroxide used)

| Curing Catalyst | Gel, Mins | Cure, Mins | Peak Exotherm, °F. | Barcol Hardness |
| --- | --- | --- | --- | --- |
| 3-Hydroxy-1,1-dimethyl-butyl Peroxypivalate (I-1) | 0.10 | 1.05 | 373 | 45–50 |
| t-Butyl Peroxypivalate (A-1) | 0.50 | 1.30 | 398 | 45–50 |
| 3-Hydroxy-1,1-dimethyl-butyl Peroxyneohexanoate (I-2) | 0.20 | 1.00 | 396 | 45–50 |
| t-Butyl Peroxyneohexanoate (A-2) | 0.20 | 1.40 | 369 | 45–50 |
| 3-Hydroxy-1,1-dimethyl-butyl Peroxyneodecanoate (I-3) | 0.15 | 1.00 | 376 | 45–50 |
| t-Butyl Peroxyneodecanoate (A-4) | 0.20 | 1.30 | 370 | 45–50 |

EXAMPLE 7

82° C. SPI Exotherms of the Hydroxy-t-Alkyl Peroxyesters of this Invention Compared to Art Peroxyesters The unsaturated polyester resin and the procedure used in this example were those employed in Example 6. The prior art compounds, 3-benzoyloxy-1,1-dimethylbutyl peroxybenzoate (A-6) of U.S. Pat. No. 3,236,872 and 4-(3-hydroxy-1,1-dimethylbutyl-peroxycarbonyl)-3-hexyl-6-[7-(3-hydroxy-1,1-dimethylbutylperoxycarbonyl)heptyl] cyclohexene (A-7) of U.S. Pat. No. 4,079,074, were prepared according to the procedures outlined in the Prior art references. Although the 3-hydroxy-1,1-dimethyl-butyl peroxyesters of this invention can be prepared without appreciable contamination by the corresponding esterperoxyester (Structure C, infra) by reacting 3-hydroxy-1,1-dimethylbutyl hydroperoxide with the corresponding acid chloride, the 3-hydroxy-1,1-dimethylbutyl peroxyesters could not be prepared from 3-hydroxy-1,1-dimethylbutyl hydroperoxide and aromatic acid chlorides. In particular, attempts to prepare 3-hydroxy-1,1-dimethylbutyl peroxybenzoate (A-8) from 3-hydroxy-1,1-dimethylbutyl hydroperoxide and benzoyl chloride produced very little of the desired product, A-8. Instead, the product was mostly A-6 which meant that benzoyl chloride reacts too readily with the HO— group of 3-hydroxy-1,1-dimethylbutyl hydroperoxide and the HO— group of A-8. On the other hand the acid chlorides that are used in the processes for producing the instant invention peroxyesters surprisingly react significantly less readily with the HO-group of 3-hydroxy-1,1-dimethylbutyl hydroperoxide and the HO-group of the 3-hydroxy-1,1-dimethylbutyl peroxyesters of this invention. Thus, the hydroxy-t-alkyl peroxyesters A of this invention are the dominant reaction products.

The following Table IV summarizes the 82° C. (180° F.) SPI exotherm data when 1.0% by pure weight of various peroxyesters were used to cure the unsaturated polyester resin. The invention peroxyesters employed were 3-hydroxy-1,1-dimethylbutyl peroxy-(2-ethylhexanoate) (I-6) and 3-hydroxy-1,1-dimethylbutyl peroxyneohexanoate (I-2) whereas the prior art compounds evaluated were A-6, A-7, t-butyl peroxy-(2-ethylhexanoate) (A-9) and t-butyl peroxybenzoate (A-10).

TABLE IV

82° C. (180° F.) SPI Exotherm Data
(1% By weight of Pure Peroxyester)

| Peroxyester | Gel, Mins | Cure, Mins | Peak Exotherm, °F. | Barcol Hardness |
|---|---|---|---|---|
| I-2 | 0.2 | 1.0 | 386 | 45–50 |
| I-6 | 1.6 | 2.4 | 382 | 40–50 |
| A-9 | 5.5 | 6.7 | 388 | 45–50 |
| A-7 | 11.5 | 14.5 | 375 | 33–45 |
| A-6 | 40.4 | 53.4 | 294 | 0–40 |
| A-10 | No Gel up to 50 minutes | | | |

The results in Table IV show that the invention 3-hydroxy-1,1-dimethylbutyl peroxyesters of this invention (i.e., I-2 and I-6) were significantly more active in the unsaturated polyester resin than were the art peroxyesters as judged by shorter gel and cure times and/or by enhanced hardness [compare the results for invention peroxyester I-6 with those for prior art peroxyesters A-9, A-7, A-6 and A-10].

What is claimed is:

1. A process of polymerizing ethylenically unsaturated monomers comprising adding to the reaction mass of said monomers an initiating amount of a hydroxy-t-alkyl peroxyester of the structure

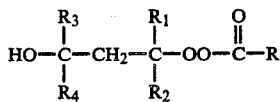

having a ten-hour half-life temperature below about 75° C., where $R_1$ and $R_2$ are selected from alkyl of 1 to 4 carbons,
$R_3$ and $R_4$ selected from hydrogen or alkyl of 1 to 4 carbons,
$R_1$ and $R_3$ can be connected together to form a lower alkyl substituted 3 carbon atom alkylene bridge and $R_3$ can additionally be

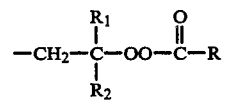

and
R is selected from

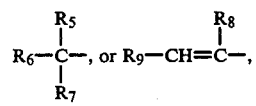

where
$R_5$ is selected from hydrogen or alkyl of 1 to 8 carbons,
$R_6$ is selected from alkyl of 1 to 8 carbons,
$R_7$ is selected from the group consisting of alkyl of 1 to 8 carbons, alkenyl of 1 to 8 carbons, alkoxy of 1 to 6 carbons, and aryloxy of 6 to 10 carbons, and
$R_8$ and $R_9$ are selected from alkyl of 1 to 4 carbons, and polymerizing said reaction mass until completion.

2. A process of curing an unsaturated polyester resin composition comprising adding to the reaction mass of said unsaturated polyester resin composition a catalyzing amount of a hydroxy-t-alkyl peroxyester of the structure

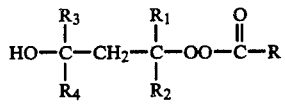

having a ten-hour half-life temperature below about 75° C., where $R_1$ and $R_2$ are selected from alkyl of 1 to 4 carbons,
$R_3$ and $R_4$ are selected from hydrogen or alkyl of 1 to 4 carbons,
$R_1$ and $R_3$ can be connected together to form a lower alkyl substituted 3 carbon atom alkylene bridge and $R_3$ can additionally be

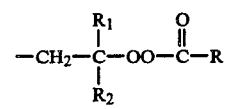

and
R is selected from

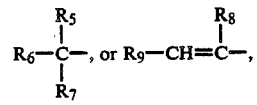

where
$R_5$ is selected from hydrogen or alkyl of 1 to 8 carbons,
$R_6$ is selected from alkyl of 1 to 8 carbons,
$R_7$ is selected from the group consisting of alkyl of 1 to 8 carbons, alkenyl of 1 to 8 carbons, alkoxy of 1 to 6 carbons, and aryloxy of 6 to 10 carbons, and
$R_8$ and $R_9$ are selected from alkyl of 1 to 4 carbons, as the curing agent and heating the reaction mass until completion.

3. The process of claim 1 wherein the ethylenically unsaturated monomer is vinyl chloride or ethylene.

4. The process of claim 3 wherein the initiator for polymerizing vinyl chloride monomer is selected from the group consisting of 3-hydroxy-1,1-dimethylbutyl peroxypivalate, 3-hydroxy-1,1-dimethylbutyl peroxyneohexanoate, and 3-hydroxy-1,1-dimethylbutyl peroxyneodecanoate.

5. The process of claim 2 wherein the curing catalyst is selected from the group consisting of 3-hydroxy-1,1-dimethylbutyl peroxypivalate, 3-hydroxy-1,1-dimethylbutyl peroxyneohexanoate, 3-hydroxy-1,1-dimethylbutyl peroxyneodecanoate, and 3-hydroxy-1,1-dimethylbutyl peroxy-2-ethylhexanoate.

* * * * *